(12) United States Patent
Guenec et al.

(10) Patent No.: US 7,354,758 B2
(45) Date of Patent: Apr. 8, 2008

(54) DEVICE AND METHOD FOR STERILITY TESTING

(75) Inventors: Oliver Guenec, Longport (FR); Eric Jallerat, Ville d'Avray (FR)

(73) Assignee: Sartorius Stedim Biotech GmbH, Goettingen (DE)

( * ) Notice: Subject to any disclaimer, the term of this patent is extended or adjusted under 35 U.S.C. 154(b) by 376 days.

(21) Appl. No.: 10/916,935

(22) Filed: Aug. 12, 2004

(65) Prior Publication Data

US 2005/0048598 A1   Mar. 3, 2005

(30) Foreign Application Priority Data

Sep. 3, 2003   (DE)   ............... 103 40 522

(51) Int. Cl.
  *C12M 1/34*   (2006.01)
  *C12M 1/12*   (2006.01)
(52) U.S. Cl. .............. 435/287.4; 435/297.2; 435/308.1; 435/309.1; 435/287.9; 210/406; 604/406; 422/101
(58) Field of Classification Search ............ 435/287.4, 435/297.2, 308.1, 309.1
  See application file for complete search history.

(56) References Cited

U.S. PATENT DOCUMENTS 4,036,698 A   7/1977   Bush et al.
4,360,435 A * 11/1982  Bellamy et al. ............ 210/636
4,777,137 A * 10/1988  Lemonnier ............... 435/288.1
5,213,967 A *  5/1993  Erdman et al. ............... 435/31

FOREIGN PATENT DOCUMENTS

EP       0 118 601 A1      9/1984
JP       2001095557 A  *   4/2001
WO     WO 03072807 A2  *   9/2003

* cited by examiner

*Primary Examiner*—William H. Beisner
(74) *Attorney, Agent, or Firm*—Anthony J. Casella; Gerald E. Hespos (57) ABSTRACT

Device and method for sterility testing, in particular of pharmaceutical products, includes a closed sterility test system having at least two test containers, in each case having an integrated test filter, an outlet connecting branch arranged below the test filter and an inlet connecting branch which is arranged above the test filter and can be connected with a tube connection via a sampling device to a sample container. The tube connection of the test container in each case has a distributing component via which a fixed tube connection to an associated nutrient medium container is formed and can be used to feed an associated nutrient medium to the test container.

21 Claims, 8 Drawing Sheets

DEVICE AND METHOD FOR STERILITY TESTING

BACKGROUND OF THE INVENTION

1. Field of the Invention

The invention relates to a device for sterility testing, in particular of pharmaceutical products, comprising a closed sterility test system having at least two test containers, in each case having an integrated test filter, an outlet connecting branch arranged below the test filter and an inlet connecting branch which is arranged above the test filter and can be connected with a tube connection via a sampling device to a sample container. The invention furthermore relates to a method for sterility testing, in particular of pharmaceutical products, in which at least two test containers of a closed sterility test system are filled with an identical sample quantity from a sample container, and the samples are filtered in the test containers, and in which, after an intermediate optional washing process, the test containers are filled with different nutrient media.

2. Description of the Related Art

Regular sterility checks are required for the use of many medicinal and pharmaceutical products. In particular, sterility tests have to be carried out in accordance with the regulations, which are specified in the pharmacopeiae, for using medicines.

In the case of the obligatory membrane filtration method for fluid medicaments—medicaments which are present in solid form may also be first of all dissolved for this using suitable means—two or more identical sample quantities are in each case fed to a test container where they are filtered by a microporous membrane having a pore size of 0.45 µm. The filtrate is then let out of the test containers and the test containers are cleaned using a sterile washing solution possibly from residues which inhibit the growth of germs. The test containers are then filled with different nutrient media, for example with thioglycolate as nutrient medium 1 and with casein soyapeptone as nutrient medium 2, and, with the inlet connecting branch closed, incubated in accordance with the valid pharmacopeiae for example "USP 25" and "EP 4", at an appropriate temperature for a predefined time, aerobically (with the air filter open) or anaerobically (with the air filter closed). In the event of contamination, a cloud-like opaqueness is formed in the (clear) nutrient fluid.

In order to carry out the sterility test, presterilized disposable sterility test systems which form a system which is closed as far as possible are preferred in order to avoid defective ("falsely positive") results. Systems of this type are known from EP 0 118 601 A1 and under the designations Steritest™ from Millipore S. A., and Sterisart® from Sartorius Ag. The Sterisart® system, which is known from Sartorius AG's brochure, comprises two transparent, cylindrical test containers with a slightly conical upwards profile which are connected to a sampling device, for example a piercing cannula, by means of a flexible double tube and a Y-distributing component. In the test containers, a respective membrane filter is clamped fixedly in a lower part of the container. The lower part of the container furthermore has a central discharge connecting branch which can be closed with a stopper. The upper part of the container has an inlet connecting branch and a vent having an integrated microporous air filter. The vent can be covered with a rubber cap. The double tube can be fitted into a pump head of a peristaltic hose pump in order to convey samples, washing solutions and nutrient media. Color-coded tube clips are prefitted on the tube connections in order to be able to close and open tube connections according to requirements.

The known sterility test system has been proven in principle. A disadvantage, however, is that it is not optimized in respect of handling with the smallest possible risk of error and in the costs for production and the testing process. In particular, after the filtration process and the washing process, the nutrient media have to be decanted successively via the sampling device into the test containers, or at least two sampling devices to which a respective tube connection to a test container is connected would be required. In order to fill the test containers with the nutrient media, separate nutrient medium containers have to be provided and connected. For this purpose, in the case of a common sampling device, the tube connection has to be connected first of all to the first nutrient medium container, then separated again from the latter and subsequently connected to the second nutrient medium container (in the case of more than two test containers and nutrient media, the process is repeated the appropriate number of times). All these working steps are relatively time-consuming, susceptible to error and conceal the risk of intermediate contamination which may lead to a false positive test result.

It is therefore the object of the present invention to improve the known sterility test system in such a manner that it is associated with a reduced risk of error, and that it is more cost-effective in production and in use.

SUMMARY OF THE INVENTION

This object is achieved according to the invention in conjunction with the subject device for sterility testing by the fact that the tube connection of the test container in each case has a distributing component via which a fixed tube connection to an associated nutrient medium container is formed and can be used to feed an associated nutrient medium to the test container.

Owing to the fact that the nutrient medium containers are integrated in the sterility test system, the risk of error during handling is reduced. The test containers are already connected to the nutrient media containers via distributing components and tube connections, so that a significant improvement in the direction of a completely closed test system is obtained. Furthermore, the test containers can be filled simultaneously and directly with the different nutrient media from the nutrient medium containers, as a result of which the expenditure of time on the sterility test can be reduced overall. Finally, the user does not have to separately order and store the nutrient media—one order number suffices for the entire system—so that outlay on purchasing and storage is reduced.

According to one preferred embodiment of the invention, the distributing components assigned to the nutrient medium containers are designed as T-components.

T-components are particularly cost-effective, and, during the production of the sterility test system, can simply be plugged onto the corresponding tube ends in a fluid-tight and sterile manner.

According to a further preferred embodiment of the invention, a flow-interrupting means is arranged in each case on the tube connection, mounted upstream of the distributing component of the nutrient medium container on the sampling-device side.

The flow-interrupting means make it possible in a simple manner to release the feed from the sample container and, after a desired sampling quantity has been removed, to block it again in order, for example, then to initiate the feed of nutrient medium.

According to a further preferred embodiment of the invention, a flow-interrupting means is provided in each case on the tube connection, adjacent to the nutrient medium container, and can be used to empty the nutrient medium container in a specific manner.

This ensures in a simple manner that the nutrient media only flow in to the tube connections when the test containers are to be filled with the nutrient media.

The above-mentioned object is also achieved according to the invention in conjunction with the subject device for sterility testing by the fact that a collecting container is connected fixedly to the outlet connecting branches of the test containers, via a distributing component and via tube connections assigned to the distributing component, so that, with the aid of flow-interrupting means arranged on the tube connections, the filtrate can be fed either to the collecting container or to an outlet.

In contrast to the previous open outlet connecting branches of the test containers, the collecting container which is integrated in the sterility test system provides a simple and sterile possibility of catching the filtered sample fluids. This is advantageous in particular in the case of expensive pharmaceutical products, for example blood derivatives, in order to be able to reuse the filtrates. In addition, the handling of the integrated collecting container is particularly simple. No separate catching containers with sterile closures have to be provided.

According to one preferred embodiment of the invention, the distributing component assigned to the collecting container is designed as an X-component, in which a flow-interrupting means is arranged on each leg of the X-component.

The X-shaped distributing component makes it possible in a particularly simple manner to catch the sample filtrate in the collecting container and to conduct the washing filtrate into the outlet.

According to a further preferred embodiment of the invention, the collecting container is designed as a flexible bag.

Flexible bags as collecting containers are particularly cost-effective, are available pre-sterilized in any desired size and take up only a small amount of space when packed.

According to a further preferred embodiment of the invention, the test containers are designed as flexible bodies. These bodies may be formed from a transparent, soft plastic material. The flexible containers may, in particular, be of cylindrical or tent-shaped design. The flexible containers may also be designed as folding bodies.

Owing to the fact that the test containers are designed as flexible bodies, the size of the packaging and therefore the costs for sales and storage are reduced. The test containers may be produced, for example, from soft PVC or from polymer or polyolefin materials and transported and stored as flat bodies in a collapsed or folded state. When they are being filled, the test containers then take on an extended shape in accordance with their construction and the degree of filling. The production costs are also reduced, since the casting molds for the conventional, different, bottle- or canister-shaped test containers are not needed. In addition, the flexible construction permits, within the rules of the pharmacopeiae, a somewhat larger filter membrane surface than the conventional, rigid containers, as a result of which the filtration duration can be shortened.

According to a further preferred embodiment of the invention, the nutrient medium containers are designed as flexible bags. The nutrient medium containers may also be designed as chamber-shaped regions in an interconnected container system.

The use of simple, flexible plastic bags as nutrient medium containers is particularly cost-effective, weight-saving and takes up little packaging space. An interconnected container system makes it possible for the sterility test system to be made even more compact.

According to a further preferred embodiment of the invention, the tube connections between the distributing components of the nutrient medium containers and the test containers can be held by a peristaltic hose pump.

The use of a hose pump for conveying the sample fluid, the nutrient fluid and the washing fluid permits a rapid conveying of a predefined quantity of fluid via one or else simultaneously a plurality of tube connections. For this purpose, the distributing components to the nutrient medium bags are arranged in such a manner and the tube lengths to the test containers are configured in such a manner that convenient insertion of the tube, or of the tubes, into the pump head of the peristaltic pump is possible.

According to a further preferred embodiment of the invention, the hose pump has a clamping position for interrupting the flow in the tube connections.

With the aid of the clamping position, the flow through the inserted tube can be interrupted. In particular, this enables flow-interrupting means which are mounted on the tube connection, upstream of the distributing component of the nutrient medium container on the sampling-device side to be omitted, which is cost-effective.

According to a further preferred embodiment of the invention, the sampling device is designed as a cannula device.

The cannula device permits a simple, sterile taking of samples. It may comprise, for example, a single needle, or a double needle. For taking samples, the needle is simply inserted into the customary plastic bottles or plastic bags having the sample fluid. In addition, a venting cannula may be provided.

According to a further preferred embodiment of the invention, the flow-interrupting means can be designed as tube clips and/or breakable flow stoppers and/or valves.

The various flow-interrupting means make it possible to control, on the various tube connections, a feed of the various fluids during the handling of the sterility test system in a manner which is comfortable, effective and cost-effective and adapted to the particular requirements.

The known methods for sterility testing have the disadvantage of not being optimized in respect of their expenditure in terms of time and costs and with regard to a low risk of error.

It is therefore a further object of the present invention to improve the known methods for sterility testing in such a manner that they operate more rapidly, cost-effectively and reliably.

This object is achieved according to the invention in conjunction with the subject method for sterility testing by the fact that the nutrient media are fed simultaneously from nutrient medium containers, which are integrated in the sterility test system via fixed tube connections, to the test containers.

The simultaneous filling of the test containers from the nutrient medium containers integrated in the sterility system makes it possible to shorten the preparation of the system for incubation purposes, and therefore the overall test time.

Intermediate working steps for changing connections between sample container and external nutrient media containers, and the insertion of a cannula into nutrient medium containers are omitted, which saves on time and costs and reduces the risk of external contaminations.

According to one preferred embodiment of the invention, the filtrate of the samples is fed to a collecting container which is mounted downstream of the test containers and is integrated fixedly in the sterility test system.

The integration of a collecting container enables an expensive filtrate to be caught in a cost-effective and reliable manner. This further reduces the costs of using the system.

Further details of the invention emerge from the following detailed description and the attached drawings, in which preferred embodiments of the invention are illustrated by way of example.

DETAILED DESCRIPTION OF THE DRAWINGS

DETAILED DESCRIPTION OF THE PREFERRED EMBODIMENTS

A device for sterility testing essentially comprises a sterility test system 1, with integrated nutrient media containers 7, 7'.

Figure 1:
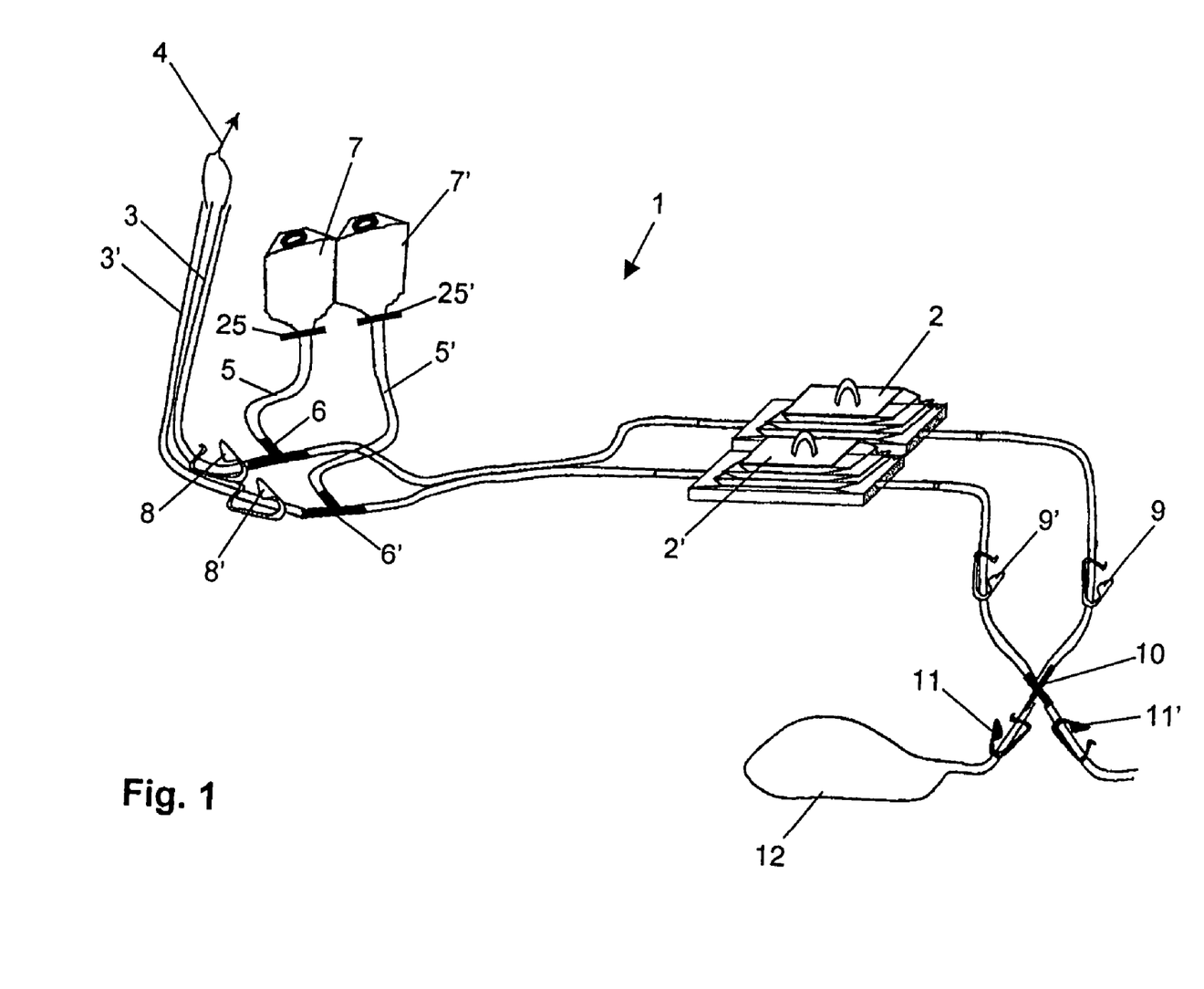
FIG. 1 shows a schematic overall illustration of a sterility test system.

FIG. 1 illustrates the complete sterility test system 1 in an overview. The system comprises two test containers 2, 2' which are connected via two tube connections 3, 3' by means of a Y-flow distributor (not illustrated) to a sampling device 4, advantageously in the form of a piercing cannula. The cannula 4 serves to remove a sample from a sample container (not illustrated). Between the sampling device 4 and the test containers 2, 2', a respective distributing component 6, 6', advantageously in the form of a T-component, is arranged in the tube connections 3, 3'. A respective fixed tube connection 5, 5' emerges from the distributing components 6, 6' and is connected to the nutrient media containers 7 and 7', respectively. The nutrient medium containers 7, 7' are assigned flow-interrupting means 25, 25', for example a breakable stopper, or a two-way directional control valve, which prevent an unintentional emptying of the containers 7, 7' into the tube connections 5, 5'. Further flow-interrupting means, advantageously two tube clips 8, 8' are provided for disconnecting the tube connections 3, 3' toward the sample container.

Figure 2:
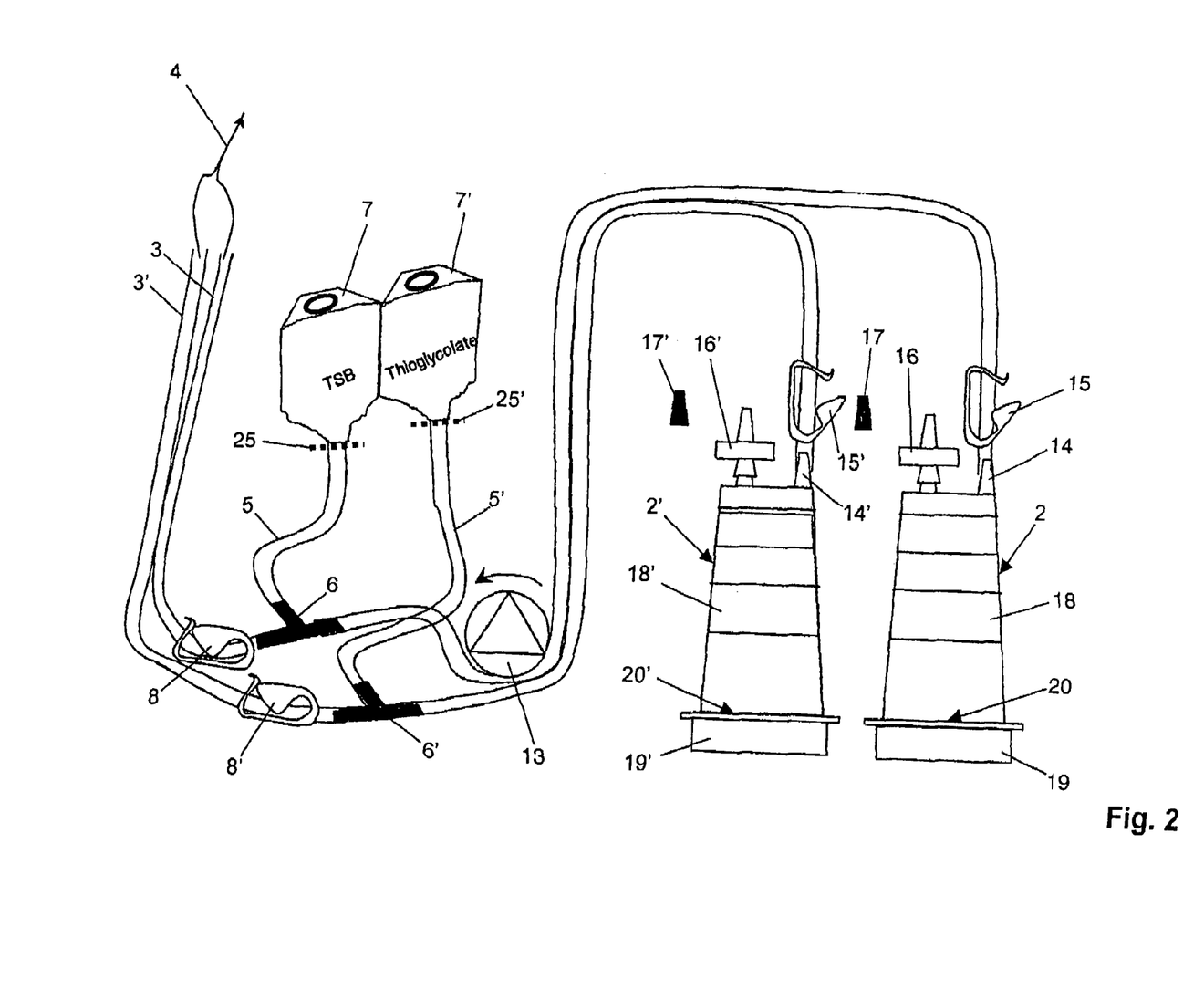
FIG. 2 shows the sterility test system in an enlarged cutout during the simultaneous filling of two test containers with two nutrient media.

Referring to FIG. 2, the test containers 2, 2' can be designed, in a construction which is known per se, as two transparent, cylindrical hard plastic containers which have a slightly conical upward profile with a container upper part 18, 18' and a container lower part 19, 19'. A respective test filter, or a filter membrane 20, 20' is fixedly clamped, in accordance with the pharmacopeiae, between the components 18, 18' and 19, 19'. The container lower part 19, 19' furthermore has a central outlet connecting branch 21, 21' (see FIG. 3) which can be closed by a stopper (not illustrated). The container upper part 18, 18' has, on the lid side, an inlet connecting branch 14, 14' and a vent with an integrated, microporous air filter 16, 16'. A tube clip 15, 15' may additionally be connected upstream of the inlet connecting branches 14, 14'. The vent or the air filter 16, 16' can be covered with a rubber cap 17, 17'.

Figure 4:
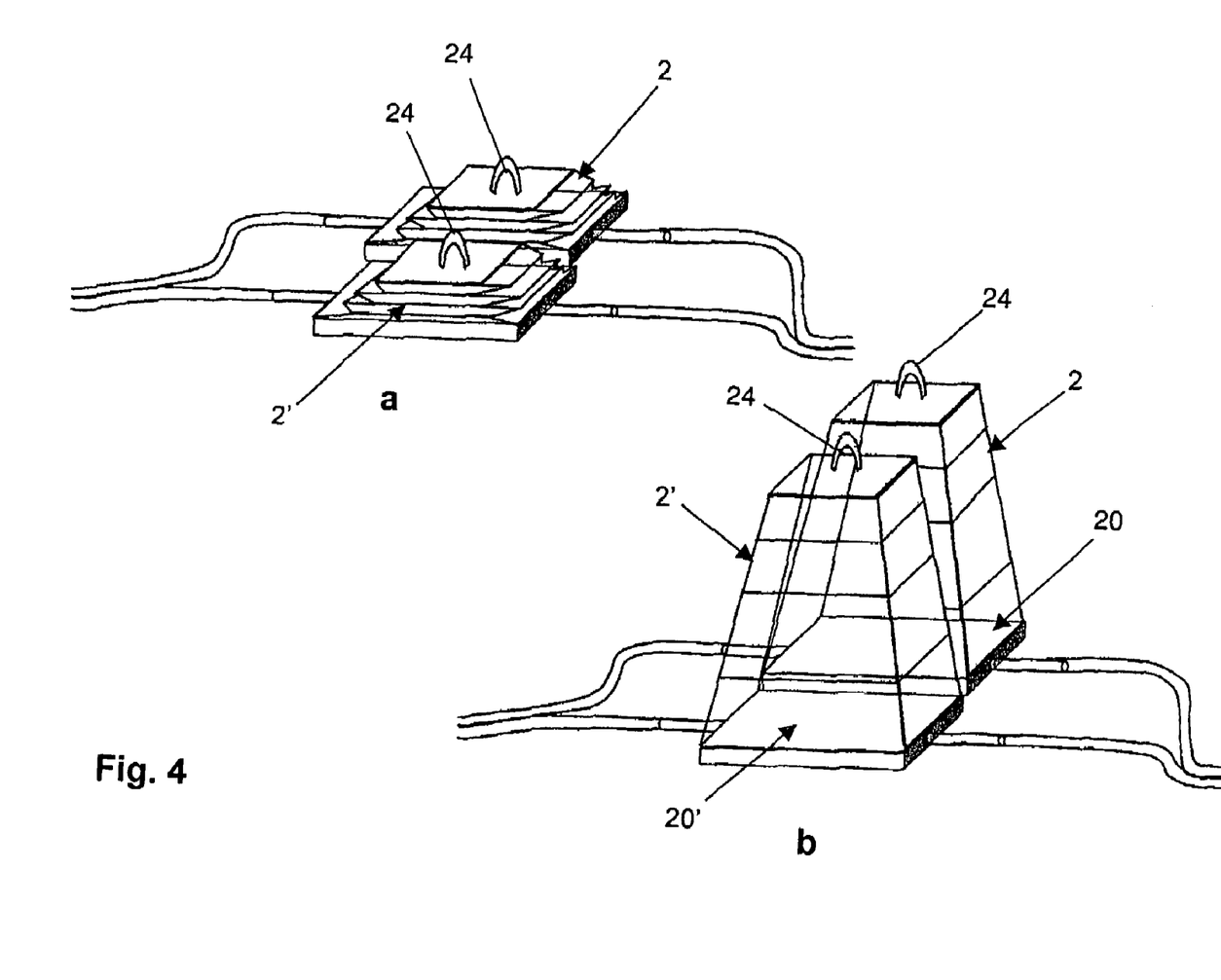
FIG. 4 shows a detailed view of two foldable test containers: (a) in a collapsed state; and (b) in an unfolded state.
Figure 7:
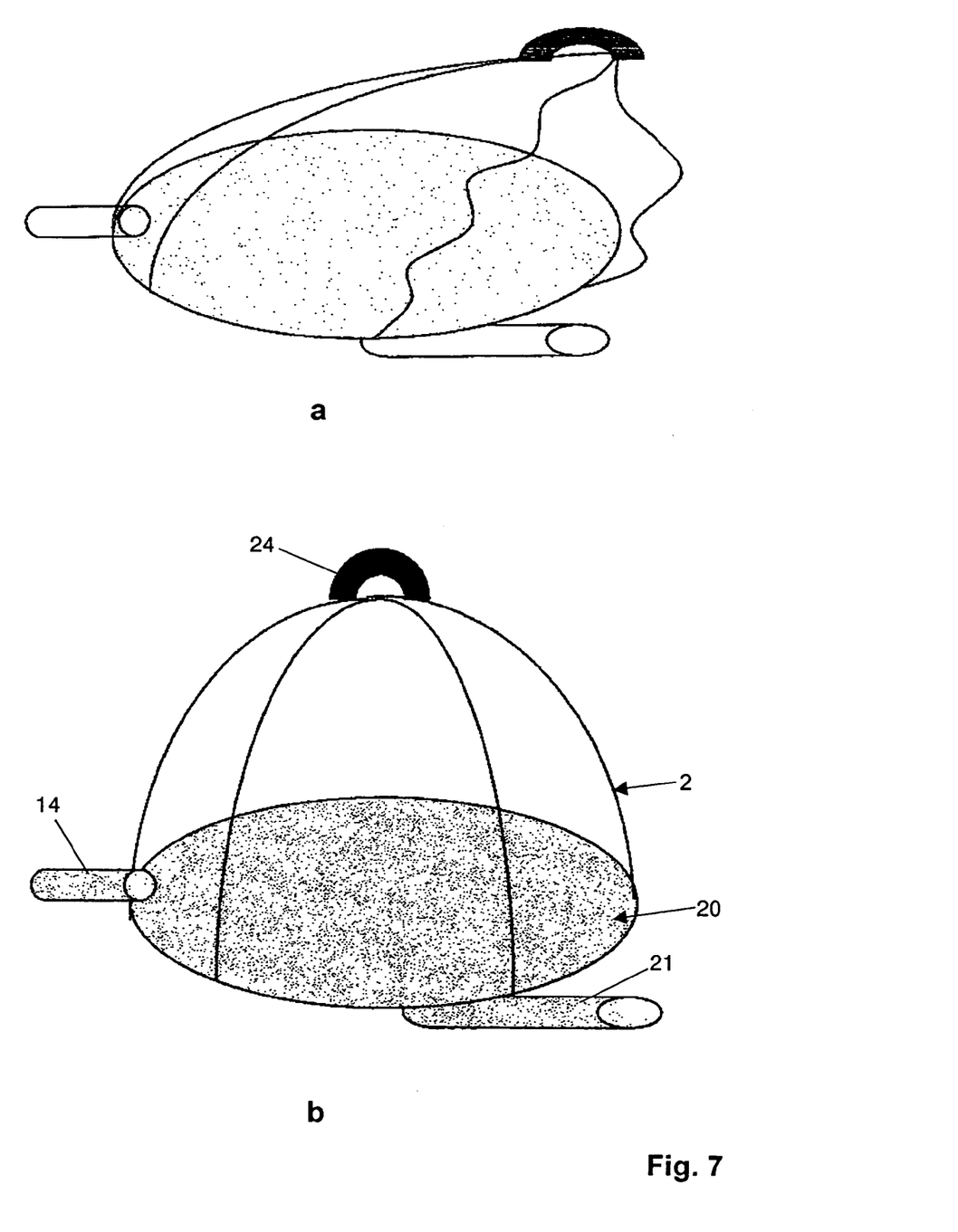
FIG. 7 shows a further design of the test container in a tent-shaped body: (a) in an empty state; and (b) in a partially filled state.
Figure 8:
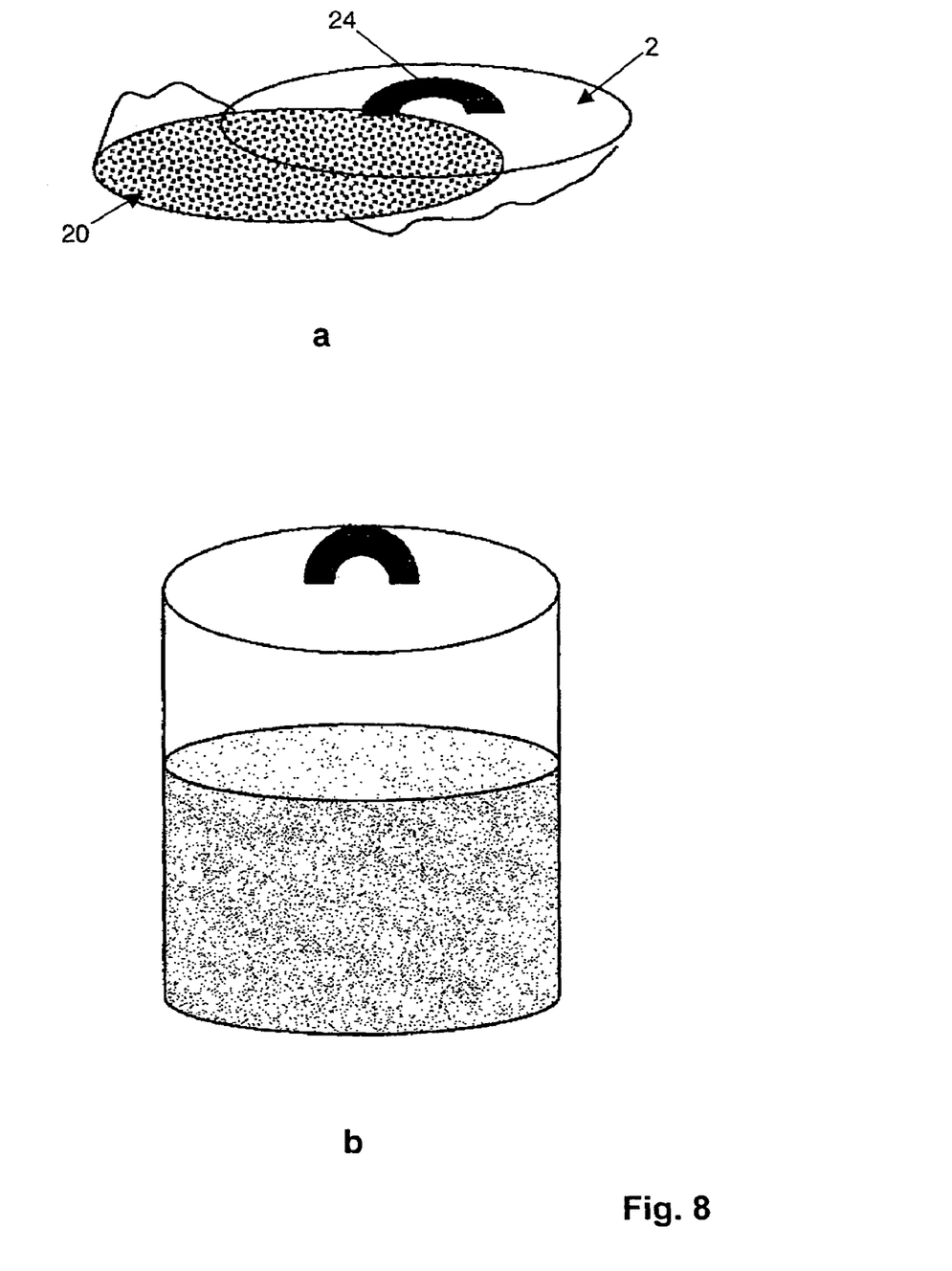
FIG. 8 shows a further design of the test container as a cylindrical body: (a) in an empty state; and (b) in a partially filled state.

In one embodiment which is illustrated in FIG. 4, the test containers 2, 2' are designed as folding bodies, preferably made from a transparent soft plastic. FIG. 4a illustrates the folding bodies in a folded state, and FIG. 4b illustrates them in an expanded state. The folding bodies have a rectangular base area into which the membrane 20, 20' is fitted. The inlet connecting branches 14, 14' and outlet connecting branches 21, 21', and the feedings and removals by the tube connections can be arranged, particularly in a manner saving on construction space, laterally on the bottom parts of the folding bodies, the inlet connecting branch 14, 14', of course, being arranged above the test filter 20, 20' and the outlet connecting branch 21, 21' being arranged below the test filter 20, 20'. A handle component 24 is formed in each case on the upper lid region for easy handling. Further embodiments of the test containers 2 as tent-shaped bodies, or as cylindrical bodies are shown in FIGS. 7 and 8, the containers 2 being illustrated in each case in an empty, collapsed state a) and in a partially filled, expanded state b).

The double tube 3, 3' can be inserted into a pump head (not illustrated) of a peristaltic hose pump 13 in order to convey samples, washing solution and nutrient media. For this purpose, the connecting parts of the double tube 3, 3' between the T-components 6, 6' and the test containers 2, 2' are designed in a length sufficient in order to ensure comfortable and secure handling. The pump head may also have a clamping position for interrupting the flow.

Figure 3:
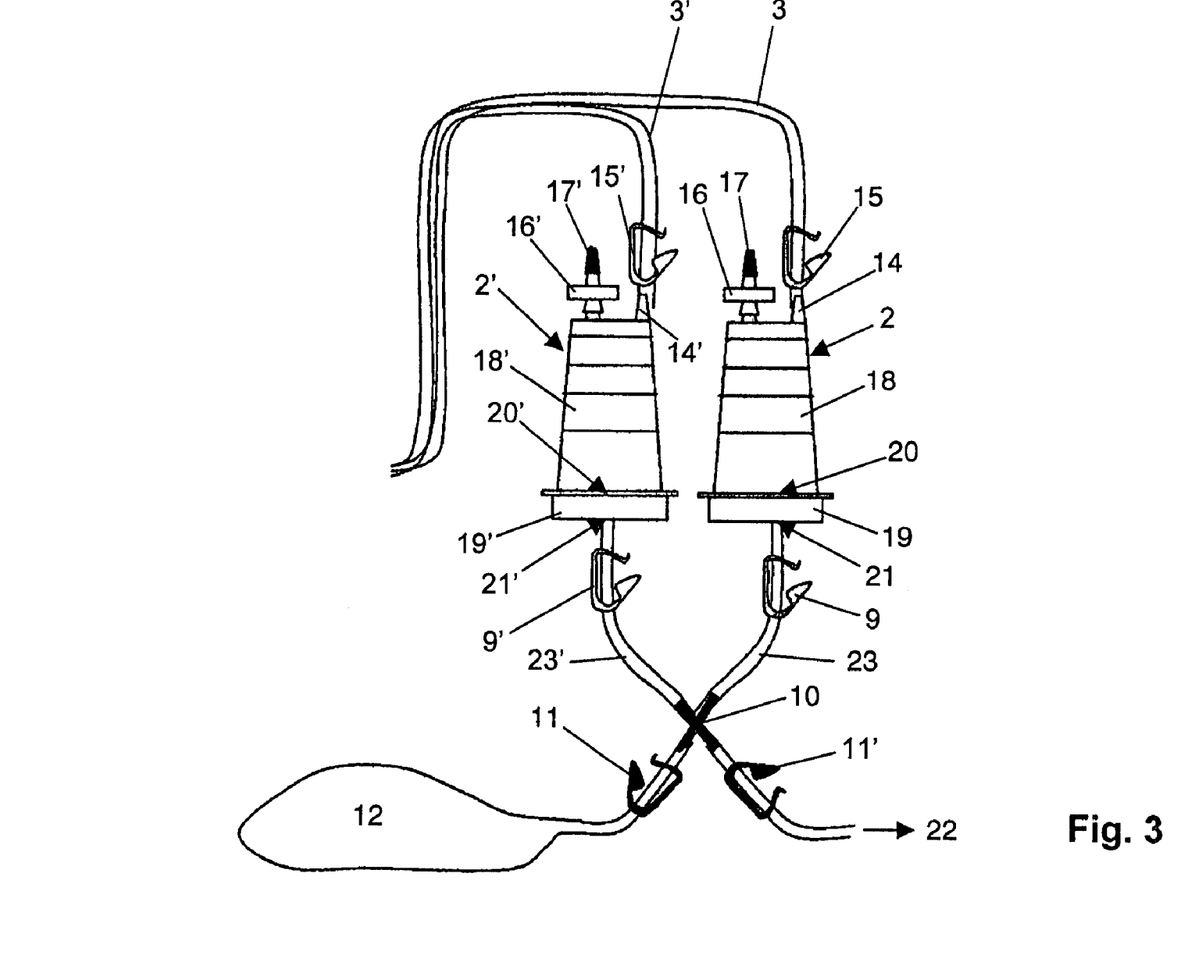
FIG. 3 shows a detailed view of the test containers together with a collecting container.

A collecting container 12, preferably designed as a flexible, sterile bag, can be connected fixedly to the outlet connecting branches 21, 21', as illustrated in FIG. 3. The collecting container 12 is fixedly connected to the outlet connecting branches 21, 21' via a distributing component 10, preferably designed as an X-component, and via tube connections 23, 23'. Tube clips 9, 9', and 11, 11' are prefitted on each leg of the X-component, advantageously in color-coded form, in order to be able to close and open the tube connections 23 and 23' as required. An outlet 22 which remains free is provided on an open side of the distributing component 10.

A method for sterility testing, of pharmaceutical fluids, is essentially based on the fact that nutrient media are simultaneously supplied to test containers 2, 2' from nutrient media containers 7, 7', which are integrated in a sterility test system 1 via fixed tube connections 5, 5'.

Figure 5:
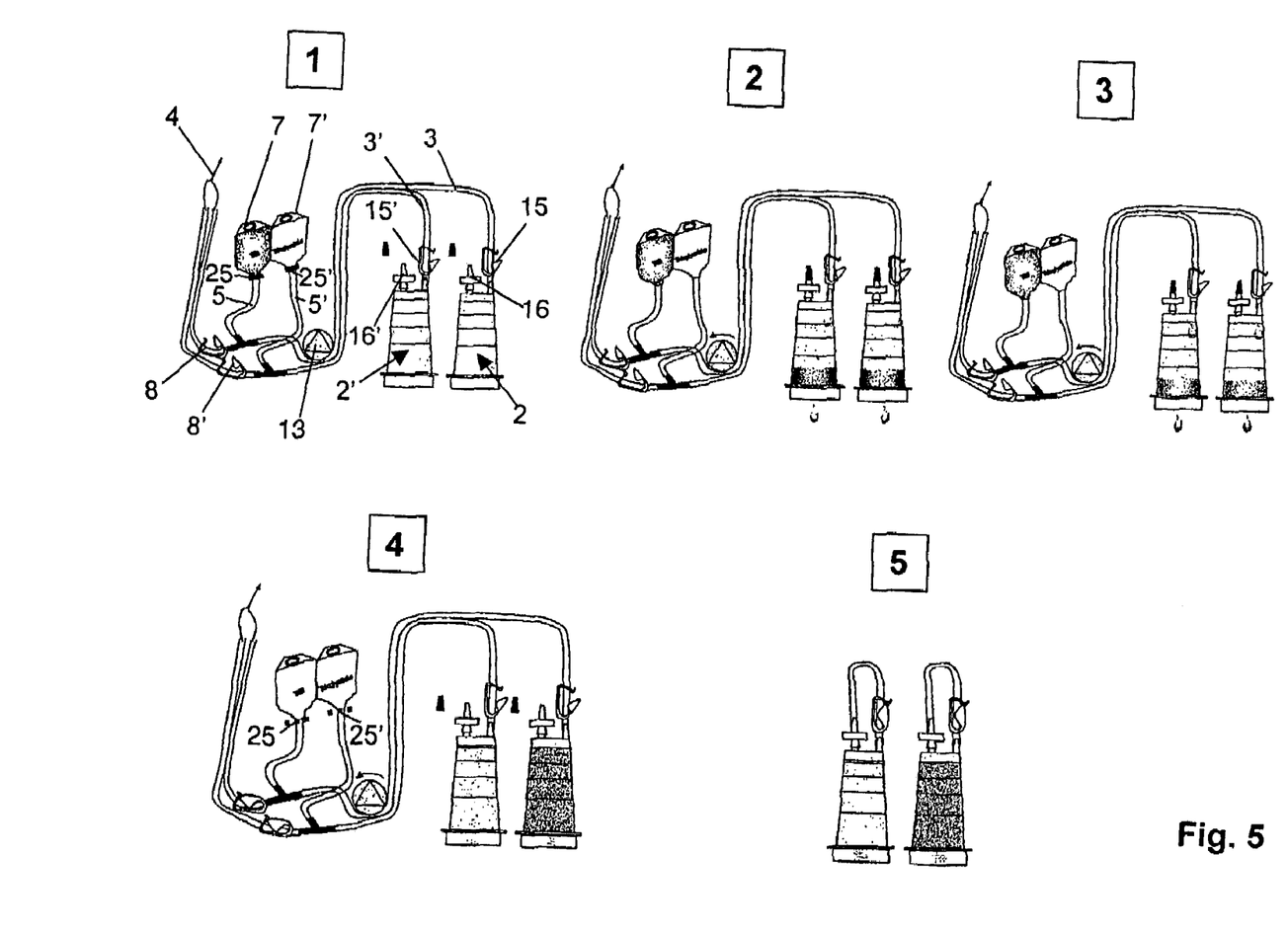
FIG. 5 shows a flow diagram of a sterility test in five individual illustrations.

The method can advantageously be carried out with the above-described device, as illustrated in the flow diagram in FIG. 5.

FIG. 5-1 shows the sterility test system 1 after removal from the packaging together with the integrated nutrient media containers 7, 7', filled with different nutrient media (TSB and thioglycolate), and with the double tube 3, 3' inserted into the pump head of the peristaltic hose pump 13. The tube clips 8, 8' and 15, 15' are open.

FIG. 5-2 shows the system during the taking of the sample and the filtration of the sample. The hose pump 13 conveys two identical sampling quantities into the test containers 2, 2' where they are filtered by the test filter 20, 20'. The filtrate runs off via the outlet connecting branches 21, 21'. FIG. 5-3 indicates a washing process, in which the containers 2, 2' and the membranes 20, 20' are cleansed of residues. FIG. 5-4 shows the simultaneous filling according to the invention of the test containers 2, 2' with the nutrient media. In this case, the tube connections 3, 3' toward the sampling device 4 are blocked by the tube clips 8, 8', and the flow-interrupting means 25, 25' are opened, so that, with the aid of the hose pump 13, the nutrient media containers 7, 7' empty simultaneously into the test containers 2, 2'. Finally, FIG. 5-5 shows the system prepared for incubation. The tube connections 3, 3' are capped, and the free ends are placed onto the openings of the air filters 16, 16' and, in addition, the tube clips 15, 15' are closed. As a result, the containers 2, 2' are hermetically sealed (anaerobic incubation).

Figure 6:
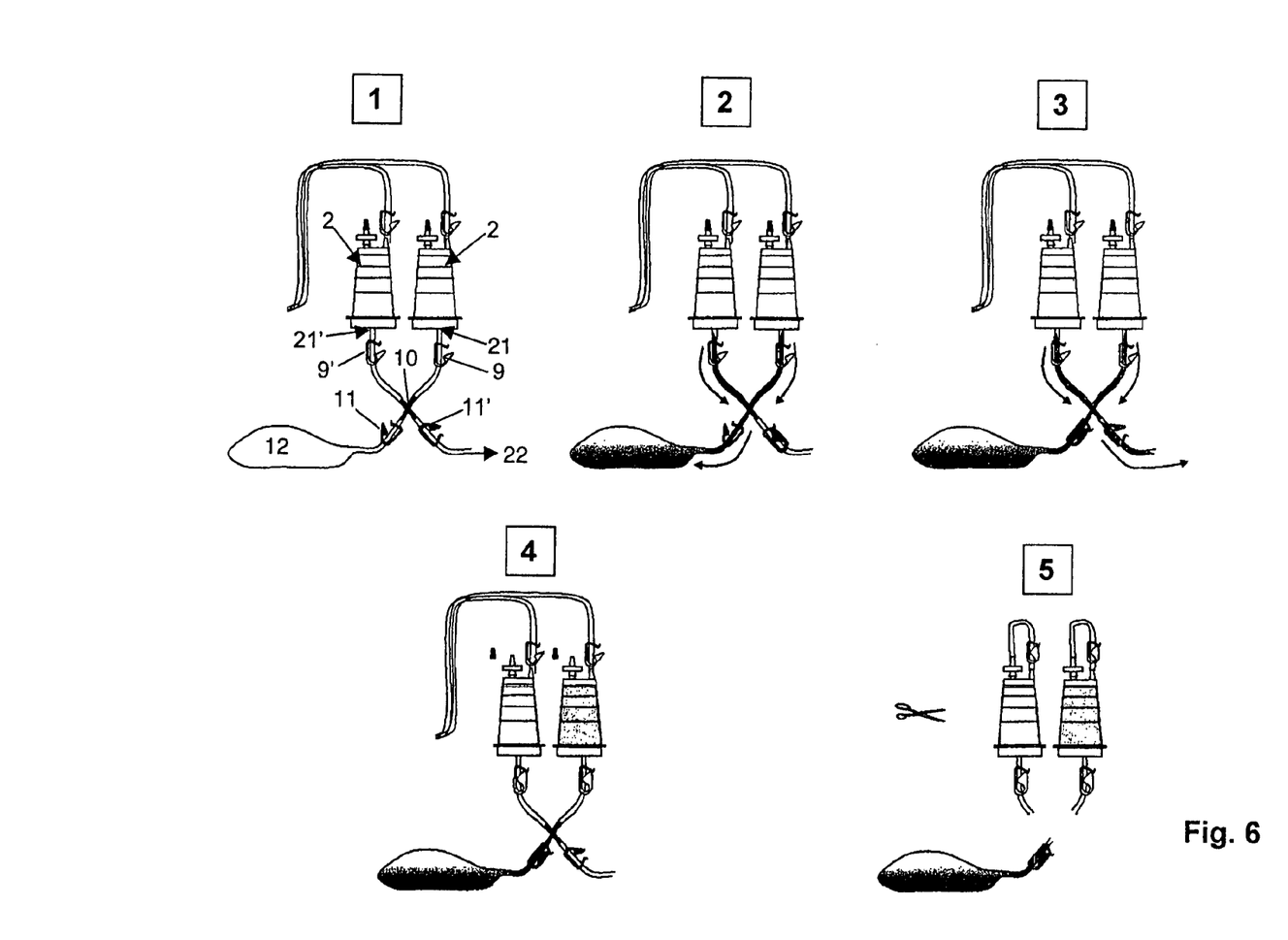
FIG. 6 shows the flow diagram with a filtrate being caught.

A further flow diagram for illustrating the method together with an integrated collecting container 12 is illustrated in FIG. 6. The manner of procedure corresponds to that of FIG. 5. However, here the filtrate of the sample is conducted into the collecting container 12 (FIG. 6-2). For this purpose, the clip 11 toward the collecting container 12 is opened and the clip 11' toward the outlet 22 is closed. By contrast, the filtrate of the washing solution is let out via the outlet 22 (FIG. 6-3). Before the test containers 2, 2' are filled with the nutrient media, the two clips 9, 9' and the clip 11 are closed (FIG. 6-4). Finally, the collecting container 12 is separated off (FIG. 6-5). The filtrate which has been decanted in sterile form is then available for further utilization.

LIST OF REFERENCE NUMBERS

| | |
|---|---|
| 1 | Sterility test system |
| 2, 2' | Test container |
| 3, 3' | Tube connection |
| 4 | Sampling device |
| 5, 5' | Tube connection |
| 6, 6' | Distributing component |
| 7, 7' | Nutrient media container |
| 8, 8' | Flow-interrupting means |
| 9, 9' | Flow-interrupting means |
| 10 | Distributing component |
| 11, 11' | Tube clip |
| 12 | Collecting container |
| 13 | Hose pump |
| 14, 14' | Inlet connecting branch |
| 15, 15' | Flow-interrupting means |
| 16, 16' | Air filter |
| 17, 17' | Covering cap |
| 18, 18' | Container upper part |
| 19, 19' | Container lower part |
| 20, 20' | Test filter |
| 21, 21' | Outlet connecting branch |
| 22 | Outlet |
| 23, 23' | Tube connection |
| 24 | Handle component |
| 25, 25' | Flow-interrupting means |

What is claimed is:

1. A kit for sterility testing of a sample container, in particular of pharmaceutical products, comprising a closed sterility test system having one sampling device, a Y-flow distributor, at least two test containers, each test container having an integrated test filter, an outlet connecting branch arranged below the test filter, and an inlet connecting branch which is arranged above the test filter and is connected with a tube connection via said sampling device to said sample container, wherein said sampling device is connected to said Y-flow distributor, and said Y-flow distributor is connected to each said tube connection (3, 3'), wherein each said tube connection (3, 3') of a test container (2, 2') has a distributing component (6, 6') and a fixed tube connection (5, 5') connected to a container having nutrient medium therein (7, 7'), that is used to feed an associated nutrient medium to the test container (2, 2'); wherein said distributing component (6, 6') and said container having nutrient medium therein (7, 7') are downstream of said sample container and sampling device.

2. The kit as claimed in claim 1, wherein the distributing components (6, 6') assigned to the container having nutrient medium therein (7, 7') are designed as T-components.

3. The kit as claimed in claim 1, wherein a flow-interrupting means (8, 8') is arranged in each case on the tube connection (3, 3'), mounted upstream of the distributing component of the container having nutrient medium therein (7, 7') on the sampling-device side.

4. The kit as claimed in claim 1, wherein a flow-interrupting means (25, 25') is provided in each case on the tube connection (5, 5') adjacent to the container having nutrient medium therein (7, 7'), and may be used to empty the nutrient medium container (7, 7') in a specific manner.

5. The kit as claimed in claim 1, wherein a collecting container (12) is connected fixedly to outlet connecting branches (21, 21') of the test containers (2, 2'), via a second distributing component (10) and via tube connections (23, 23') assigned to the distributing component (10), so that, with the aid of flow-interrupting means (9, 9'11, 11') arranged on the tube connections (23, 23'), the filtrate can be fed either to the collecting container (12) or to an outlet (22).

6. The kit as claimed in claim 5, wherein the distributing component (10) assigned to the collecting container (12) is designed as an X-component, in which a flow-interrupting means (9, 9'11, 11') is arranged on each leg of the X-component.

7. The kit as claimed in claim 6, wherein at least one flow-interrupting means (8, 8', 9, 9', 11, 11', 15, 15', 25, 25') is designed as a tube clip.

8. The kit as claimed in claim 6, wherein at least one flow-interrupting means (8, 8', 9, 9', 11, 11', 15, 15', 25, 25') is designed as a breakable flow stopper.

9. The kit as claimed in claim 6, wherein at least one flow-interrupting means (8, 8', 9, 9', 11, 11', 15, 15', 25, 25') is designed as a valve.

10. The kit as claimed in claim 5, wherein the collecting container (12) is designed as a flexible bag.

11. The kit as claimed in claim 1, wherein the test containers (2, 2') are designed as a flexible bodies.

12. The kit as claimed in claim 11, wherein the flexible bodies are formed from a transparent, soft plastic material.

13. The kit as claimed in claim 11, wherein the test containers (2, 2') are designed as a folding bodies.

14. The kit as claimed in claim 11, wherein the test containers (2, 2') are designed as cylindrical bodies.

15. The kit as claimed in claim 11, wherein the test containers (2, 2') are designed as tent-shaped bodies.

16. The kit as claimed in claim 1, wherein the container having nutrient medium therein (7, 7') are designed as a flexible bag.

17. The kit as claimed in claim 16, wherein the container having nutrient medium therein (7, 7') are designed as chamber-shaped regions in an interconnected container system.

18. The kit as claimed in claim 1, wherein the tube connections (3, 3') between the distributing components (6, 6') of the container having nutrient medium therein (7, 7') and the test containers (2, 2') can be held by a peristaltic hose pump (13).

19. The kit as claimed in claim 18, wherein the hose pump (13) has a clamping position for interrupting the flow in the tube connections (3,3').

20. The kit as claimed in claim 1, wherein the sampling device (4) is designed as a cannula device.

21. A kit for sterility testing of a sample container, in particular of pharmaceutical products, comprising a closed sterility test system having one sampling device, a Y-flow distributor, at least two flexible or foldable test containers, each test container having an integrated test filter, an outlet connecting branch arranged below the test filter, and an inlet connecting branch which is arranged above the test filter and is connected with a tube connection via said sampling device to said sample container, wherein said sampling device is connected to said Y-flow distributor, and said Y-flow distributor is connected to each said tube connection (3, 3'), wherein each said tube connection (3, 3') of a flexible or foldable test container (2, 2') has a distributing component (6, 6') and a fixed tube connection (5, 5') connected to a flexible container having nutrient medium therein (7, 7'), that is used to feed an associated nutrient medium to the test container (2, 2'); wherein said distributing component (6, 6') and said flexible container having nutrient medium therein (7, 7') are downstream of said sampling container and sampling device; and wherein a collecting container (12) is connected fixedly to outlet connecting branches (21, 21') of the test containers (2, 2'), via a second distributing component (10) and via tube connections (23, 23') assigned to the distributing component (10), so that, with the aid of flow-interrupting means (9, 9', 11, 11') arranged on the tube connections (23, 23'), the filtrate can be fed either to the collecting container (12) or to an outlet (22).

* * * * *